United States Patent [19]

Evans et al.

[11] Patent Number: 5,520,174

[45] Date of Patent: May 28, 1996

[54] TRACHEOSTOMY TUBE GUARD

[76] Inventors: Larry L. Evans; Michael P. Rosiak; Brian M. Toal, all of c/o RET Medical, 1831-R E. Chocolate Ave., Hershey, Pa. 17033

[21] Appl. No.: 195,089

[22] Filed: Feb. 14, 1994

[51] Int. Cl.$^6$ .................................................. A61M 16/00
[52] U.S. Cl. ............. 128/207.14; 128/912; 128/DIG. 26
[58] Field of Search ......................... 128/200.26, 207.14, 128/207.15, 207.16, 912, DIG. 26

[56] References Cited

U.S. PATENT DOCUMENTS

| | | | |
|---|---|---|---|
| D. 309,021 | 7/1990 | Beevers | D24/51 |
| 4,332,143 | 5/1982 | Foster | 128/207.17 |
| 4,363,320 | 12/1982 | Kossove | 128/207.14 |
| 4,435,174 | 3/1984 | Redmond et al. | 604/174 |
| 4,588,399 | 5/1986 | Nebergall et al. | 604/280 |
| 4,683,879 | 8/1987 | Williams | 128/200.26 |
| 4,796,617 | 1/1989 | Matthews et al. | 128/204.25 |
| 4,802,474 | 2/1989 | Beevers | 128/200.26 |
| 4,896,667 | 1/1990 | Magnuson et al. | 128/207.14 |
| 4,909,248 | 3/1990 | Anderson | 128/207.14 |
| 5,009,227 | 4/1991 | Nieuwstad | 128/207.17 |
| 5,067,496 | 11/1991 | Eisele | 128/207.15 |
| 5,124,129 | 6/1992 | Riccitelli et al. | 422/56 |
| 5,201,309 | 4/1993 | Friberg et al. | 128/207.14 |

*Primary Examiner*—Aaron J. Lewis
*Attorney, Agent, or Firm*—Richard C. Litman

[57] ABSTRACT

A guard for preventing occlusion of a tracheostomy tube. The guard includes a ring for slipping over the exposed end of the tracheostomy tube, thereby securing the guard to the tube, and a visor-like extension or guard which projects forwardly of and above the tube open end, thus being in a position to fend off an object which threatens to block the tube open end. The guard includes grips enabling sure grasp thereof to facilitate handling by medical personnel, as during removal and replacement of the tube. An opening is formed in the extension, so that in the event the guard rotates about the tube, and the extension is moved from its original location above the tube opening to a new location therebelow, a secondary airway is established. This will enable a patient to continue breathing, even if an object is sufficiently near the tube opening as to partially obstruct the same. Because a significant number of fatalities result when a patient's head slumps forward, the chin settling upon and obstructing the tube opening, the invention finds greatest application to those having neurological disorders, spinal injuries, and other ailments which reduce control of the head.

2 Claims, 1 Drawing Sheet

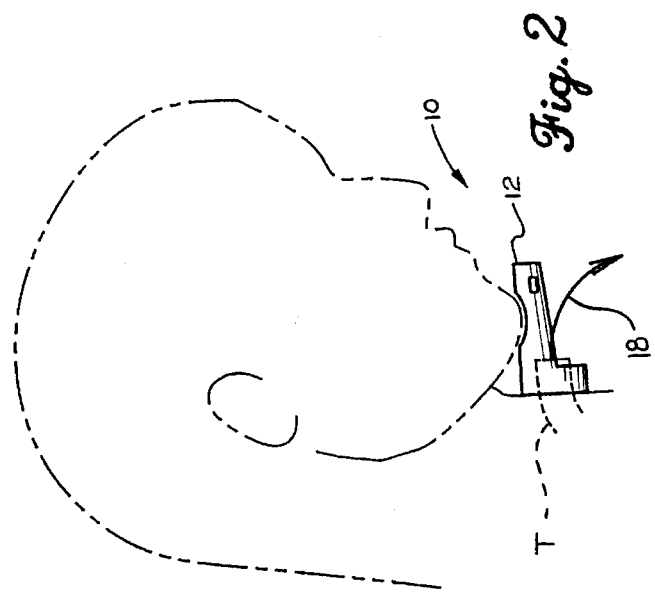
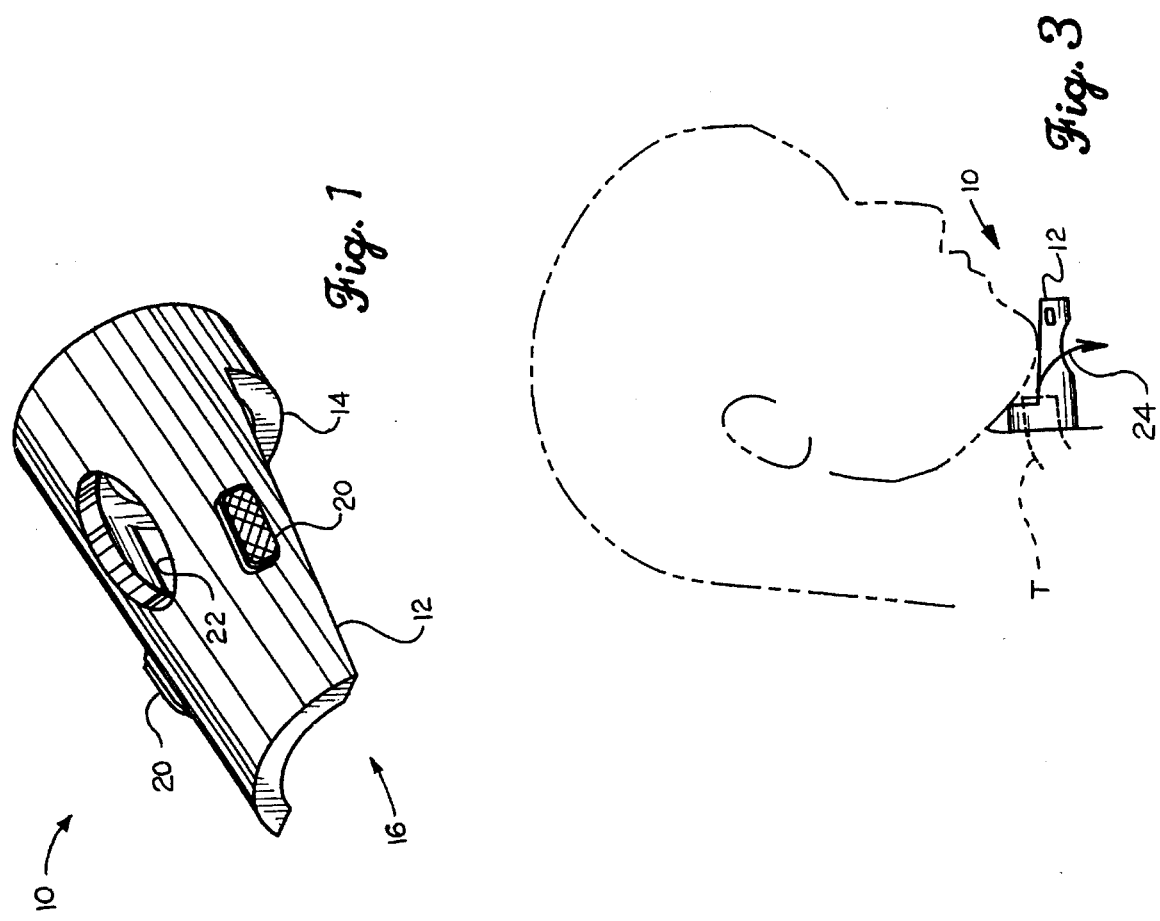

TRACHEOSTOMY TUBE GUARD

BACKGROUND OF THE INVENTION

1. Field of the Invention

The present invention relates to a guard for opposing occlusion of a tracheostomy tube.

2. Description of the Prior Art

Tracheal tubes are by their nature subject to hazards which could block their effectiveness. These tubes may be displaced, collapsed, bitten through, and otherwise disturbed. Many prior art devices have been developed to overcome these problems. Most such devices include a substantially tubular member for attachment to a tracheal tube.

A device specifically for preventing occlusion of the open end of a tracheostomy guard is seen in U.S. Pat. Nos. 4,802,474 and Des. 309,021, both issued to Katherine K. Beevers on Feb. 7, 1989 and Jul. 3, 1990, respectively. The device includes a cage which covers the open end of the tracheostomy tube.

U.S. Pat. No. 4,896,667, issued to Linda M. Magnuson et al. on Jan. 30, 1990, discloses a bite block for an endotracheal tube. This bite block includes a generally cylindrical, hollow body which is slotted longitudinally. A coaxial extension forming a trough or chute projects from the body. Short slots are formed in the body for accepting a tape for securing the bite block in place on a person's body.

U.S. Pat. No. 5,009,227, issued to Peter P. Nieuwstad on Apr. 23, 1991, discloses an endotracheal tube holder having a harness encircling a patient's head, and a generally tubular support member. The tubular support member is characterized by two wings which extend radially therefrom, for attachment to the harness. The tubular member is hollow, for allowing passage of an endotracheal tube. A second, parallel, passageway is provided for supporting a feeding tube.

A dual purpose connector for endotracheal apparatus is seen in U.S. Pat. No. 4,683,879, issued to R. Tudor Williams on Aug. 4, 1987. The connector, which has a generally tubular central body, is attachable to tubes at both ends. Also, a slot enables penetration into the passageway of additional equipment. Illustratively, this additional equipment could include a supply tube for introducing anaesthetizing gas into the central passageway, an optic probe for observation, and the like. The central body is formed in parts of different diameters, the portion of larger diameter having a flange for facilitating connection of one or more associated endotracheal tubes. A longitudinal slot enables entry of the additional equipment which can be employed with this invention.

A catheter guide is described in U.S. Pat. No. 4,435,174, issued to Russell J. Redmond et al. on Mar. 6, 1984. A J-shaped tube attaches at the long, straight portion of the J to a circular flange. The axis of the tube is parallel to the plane of the circular flange. The external portion of the elbow of the J-shape is removed to provide a slot enabling insertion of a tube into the catheter guide.

U.S. Pat. No. 4,363,320, issued to Michael Kossove on Dec. 14, 1982, concerns a breathing apparatus for holding a tube for breathing tubes, catheters and the like which is formed in two parts. An outer, tubular member encloses an interior member which is configured to occupy the interior of the outer member. The interior member has a central wall arranged to divide the open interior of the outer member into two passageways, and an outer, circumferential wall. The outer, circumferential wall is not continuous, which configuration would cause the inner member to be tubular, due to two longitudinal slots. These slots, in combination with the central wall and the partial circumferential wall, cause the inner member to form a pair of back-to-back, mirror image C-shapes. The inner member reinforces the flexible outer member.

U.S. Pat. No. 4,331,143, issued to Billy R. Foster on May 25, 1982, discloses a head harness which supports an arcuate member for fastening to an endotracheal tube. The endotracheal tube is suspended from the arcuate member.

U.S. Pat. No. 5,124,129, issued to Samuel D. Riccitelli et al. on Jun. 23, 1992, is directed toward an indicator of carbon dioxide in exhaled air. A connector having coaxial tubular members of large and smaller diameters includes a flange radiating outwardly at the juncture of the two tubular members. The device senses carbon dioxide by a dye suspended in the material from which the device is made, the dye reacting to a combination of water vapor and carbon dioxide.

Another connector having members of coaxial members of different diameters is seen in U.S. Pat. No. 4,796,617, issued to Hugoe R. Matthews et al. on Jan. 10, 1989. The connector has a central portion including an opening for insertion of gas tubes and the like.

U.S. Pat. No. 5,067,496, issued to Robert F. Eisele on Nov. 26, 1991, discloses a tracheostomy tube which attaches to other supply tubes, and includes an inflatable cuff for sealing the incision in a patient.

U.S. Pat. No. 4,588,399, issued to Perry A. Nebergall et al. on May 13, 1986, discloses a cannula including a plurality of mutually attaching tubes, one of which has a longitudinal slot, serving as a alternative vent opening in the event of clogging of the main egress opening.

None of the above inventions and patents, taken either singly or in combination, is seen to describe the instant invention as claimed.

SUMMARY OF THE INVENTION

While the proper support and protection of fluid supplying and breathing tubes inserted into the body of a patient is a recognized need addressed in the prior art, a particular area of concern focuses on unobstructed operation of tracheostomy tubes. The prior art cited above applies generally to all tracheal tubes, there being certain common structural features thereamong. It is the purpose of the present invention to prevent occlusion of, specifically, a tracheostomy tube.

In contrast to endotracheal tubes, a tracheostomy tube enters the body below the chin, generally opening to the atmosphere at that point. Certain classes of medical patients are particularly susceptible to self-induced occlusion. Among patients having neurological disorders, spinal injuries, and other ailments affecting, in particular, support of the head, it is not infrequent that the head slumps over, causing the chin to cover the opening of the tracheostomy tube. Other occurrences which can also cause occlusion include the drawing close of a blanket or pillow during sleep. Any such event occurring during sleep or unconsciousness becomes a threat to survival, and some cases of fatality are now attributed to such occlusion.

Clearly, occlusion of this nature is not the severe problem to an endotracheal tube, which passes through a patient's mouth, that it is to a tracheostomy tube, which is inserted into an incision below the chin.

The present invention provides a tracheostomy tube guard including a member for securement to the end of a tracheostomy tube, and a guard for preventing occlusion thereto, as by the chin covering the same. The guard is in the form of a visor, normally oriented such that it projects above the tube opening.

Since it is possible that the tube guard will be inadvertently rotated, so that the guard projects below the tube opening, a bypass ventilation opening is provided in the visor-like guard member. If rotation does indeed occur, and the patient's head slumps forwardly, the chin will be stopped by the guard, and an impromptu air passageway will remain open.

The tracheostomy tube guard also has ridges or the like formed in the body, for increasing friction for medical personnel to grasp the device during replacement of a tracheostomy tube. Since the tube guard can be made from materials such as nylon, smooth external walls may be difficult to grasp securely, and enhancement of grasp leads to more efficient handling thereof.

Accordingly, it is a principal object of the invention to provide a tracheostomy tube guard which has a member fending off the patient's chin or other object which may block a tracheostomy tube opening.

It is another object of the invention to provide a tracheostomy tube guard which is downwardly open, so that a breathing airway is established in a path directed away from the chin.

It is a further object of the invention to provide a tracheostomy tube guard which includes structure establishing a secondary breathing airway in the event that the guard moves from its initial, upward orientation.

Still another object of the invention is to provide a tracheostomy tube guard having an enhanced gripping surface, so that medical personnel can manipulate the guard with sure, confident grip.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a perspective view of the invention.

FIG. 2 is an environmental, diagrammatic, side elevational view of the invention, showing the novel guard operating in its intended position, drawn to reduced scale.

FIG. 3 is a view comparable to FIG. 2, illustrating continued effectiveness of the invention even when operating in an unintended position.

Similar reference characters denote corresponding features consistently throughout the attached drawings.

DETAILED DESCRIPTION OF THE PREFERRED EMBODIMENT

Turning now to FIG. 1 of the drawings, the present tracheostomy tube guard 10 is seen to be of unitary construction and includes an arcuate, visor-like or visor shaped projection portion 12 attached to ring-shaped attachment portion 14. Ring-shaped attachment portion 14 is slipped over an exposed end of a tracheostomy tube T, as clearly seen in FIGS. 2 and 3, and secures tube guard 10 to tube T by partially surrounding and frictionally gripping the same.

Arcuate projection portion 12 extends forwardly and at the top of the tube opening from ring-shaped attachment portion 14, defining an open channel 16 therebelow which is forward of ring-shaped attachment portion 14. This open channel 16 provides a primary breathing airway 18 (see FIG. 2) for breathing during normal operation of the invention.

Projection portion 12 is arcuate in cross section, and is shown in FIG. 1 to have a partial circular circumference. The arcuate cross section of the projection portion 12 serves two purposes. One is that a rounded shape has fewer sharp edges or corners to catch on bed clothes and the like. Another function is that depth of the trough formed within guard portion 12 is less easily obstructed, as by bed clothes, the patient's chin, or other objects which could occlude tube T if sufficiently close.

Guard 10 is provided with gripping members 20 formed therein, affording a sure and confident grip to medical personnel who must manipulate guard 10, as when adjusting or changing a tracheostomy tube. Gripping members 20 preferably project from the smooth wall of guard 10, thus engaging the fingertips of medical personnel.

As seen in FIG. 2, arcuate projection portion 12 fends off the chin of a sleeping or unconscious patient from the opening of tube T. Primary breathing airway 18 is indicated by an arrow.

It is possible that guard 10 may become unintentionally rotated such that projection portion 12 is moved from its original position above open channel 16 to a new position forward and at the bottom of ring-shaped attachment portion 14. In this position, it would be possible for a person's chin to cover the opening of tube T, and thus still suffocate the patient. To help preclude this occurrence, an aperture 22 is provided in projection portion 12 which establishes a secondary breathing airway 24, as indicated by the arrow seen in FIG. 3, Even if the patient's chin bears against tube guard 10, the arcuate shape of projection portion 12 opposes sealing off airway 24 by the chin.

Guard 10 is sufficiently uncomplicated as to lend itself to inexpensive fabrication, as by molding from inexpensive materials, such as synthetic polymers.

In a preferred embodiment, ring-shaped attachment portion 14 has an external diameter of 22 mm and an internal diameter of 16 mm. Opening 22 is preferably 1 cm in diameter, and the overall length of guard 10 is 27 mm. While these dimensions are preferred, the present invention is obviously capable of being practiced in other forms.

It is to be understood that the present invention is not limited to the sole embodiment described above, but encompasses any and all embodiments within the scope of the following claims.

We claim:

1. A unitary guard for preventing occlusion of an open end of a tracheostomy tube, comprising:

a ring-shaped attachment portion having a diameter to frictionally fit over an exposed end of a tracheostomy tube; and an arcuate, visor-shaped projection portion extending from said attachment portion, said arcuate projection portion having a partial circular circumference to define an open channel; there further being an aperture through said arcuate projection portion.

2. The guard according to claim 1, further including at least one gripping member disposed on said arcuate projection portion, whereby gripping of said at least one gripping member exerts force on said attachment portion.

* * * * *